United States Patent
Bodmer et al.

(10) Patent No.: US 6,316,227 B1
(45) Date of Patent: Nov. 13, 2001

(54) NUCLEIC ACIDS ENCODING INTERLEUKIN-5 SPECIFIC RECOMBINANT ANTIBODIES

(75) Inventors: Mark William Bodmer, South Hinksey; Diljeet Singh Athwal, London; John Spencer Emtage, Marlow, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/347,061

(22) Filed: Jul. 2, 1999

Related U.S. Application Data

(63) Continuation of application No. 08/470,139, filed on Jun. 6, 1995, now Pat. No. 5,998,586.

(30) Foreign Application Priority Data

Jun. 17, 1994 (GB) .................................................. 9412230

(51) Int. Cl.[7] .................................................. C12N 15/00
(52) U.S. Cl. ........................ 435/69.6; 435/325; 435/335; 435/372.1; 435/410; 536/23.1; 536/23.53; 536/24.1; 530/388.1; 530/388.23
(58) Field of Search ................................... 435/69.6, 325, 435/326, 328, 335, 358, 365, 372.1, 410, 243; 536/23.1, 23.53, 24.1; 530/387.1, 387.3, 388.1, 388.23

(56) References Cited

U.S. PATENT DOCUMENTS 5,585,089  12/1996  Queen et al. .

FOREIGN PATENT DOCUMENTS

| 0 120 694 | 10/1984 | (EP) . |
| 0 125 023 | 11/1984 | (EP) . |
| 0 239 400 | 9/1987 | (EP) . |
| WO 90/07861 | 7/1990 | (WO) . |
| WO 91/09967 | 7/1991 | (WO) . |
| WO 93/16184 | 8/1993 | (WO) . |

OTHER PUBLICATIONS

Begent, R.H.J. et al., "Phase I/II Study of Chimeric B72.3 Antibody in Radioimmunotherapy of Colorectal Carcinoma," *Br. J. Cancer* 1990, 62, 487.

Cockett, M. et al., "The Use of Engineered E1A Genes to Transactivate the hCMV–MIE Promoter in Permanent CHO Cell Lines," *Nucl. Acids Res.*, 1991, 19(2), 319–325.

Jones, P. et al., "Replacing the complementarity–determining regions in a human antibody with those from a mouse," *Nature*, 1986, 321, 522–525.

Kabat et al., "Sequences of Proteins of Immunological Interest," U.S. Dept. of Health and Human Services, National Institute of Health, 1987.

Kabat et al., *Sequences of Proteins of Immunological Interest*, Fifth Edition, U.S. Dept. of Health and Human Services, National Institute of Health, vol. 1, 1991.

Maniatis et al., *Molecular Cloning: A Laboratory Manual*, Second Edition, Cold Spring Harbor Laboratory Press, vols. 1–3, 1989.

Mauser, P. et al., "Effects of an Antibody to Interleukin–5 in a Monkey Model of Asthma," *Am. J. Resp. Crit. Care Med.*, 1995, 152, 467–472.

Queen et al., "A humanized antibody that binds to the interleukin 2 receptor," *Proc. Natl. Acad. Sci. USA*, 1989, 86, 10029–10033.

Riechmann et al., "Reshaping human antibodies for therapy," *Nature*, 1988, 332, 323–327.

Rudikoff et al., "Single amino acid substitution altering antigen–binding specificity," *Proc. Natl. Acad. Sci. USA*, 1982, 79, 1979–1983.

Verhoeyen, M. et al., "Reshaping Human Antibodies: Grafting an Antilysozyme Activity," *Science*, 1988, 239, 1534–1536.

*Primary Examiner*—Sheela Huff
*Assistant Examiner*—Larry R. Helms
(74) *Attorney, Agent, or Firm*—Woodcock Washburn Kurtz Mackiewicz & Norris LLP

(57) ABSTRACT

An effective anti-IL-5 recombinant antibody molecule comprising heavy and/or light chain antigen-binding residues from a donor antibody.

8 Claims, 12 Drawing Sheets

FIG.1

| | | | | | | | | | | | |
|---|---|---|---|---|---|---|---|---|---|---|---|
|GAA|TCT|GGA|GGA|GGC|TTG|GTA|CAG|CCA|TCA|CAG|ACC|
|E|S|G|G|G|L|V|Q|P|S|Q|T|

| | | | | | | | | | | | |
|---|---|---|---|---|---|---|---|---|---|---|---|
|CTG|TCT|CTC|ACC|TGC|ACT|GTC|TCT|GGG|TTA|TCA|TTA|
|L|S|L>|T|C|T|V|S|G|L|S|L|

| | | | | | | | | | | | |
|---|---|---|---|---|---|---|---|---|---|---|---|
|ACC|AGC|AAT|AGT|GTG|AAC|TGG|ATT|CGG|CAG|CCT|CCA|
|T|S|N|S|V|N>|W|I|R|Q|P|P|

| | | | | | | | | | | | |
|---|---|---|---|---|---|---|---|---|---|---|---|
|GGA|AAG|GGT|CTG|GAG|TGG|ATG|GGA|CTA|ATA|TGG|AGT|
|G|K|G|L|E|W|M|G|L>|I|W|S|

| | | | | | | | | | | | |
|---|---|---|---|---|---|---|---|---|---|---|---|
|AAT|GGA|GAC|ACA|GAT|TAT|AAT|TCA|GCT|ATC|AAA|TCC|
|N|G|D|T|D|Y|N|S|A|I|K|S>|

| | | | | | | | | | | | |
|---|---|---|---|---|---|---|---|---|---|---|---|
|CGA|CTG|AGC|ATC|AGT|AGG|GAC|ACC|TCG|AAG|AGC|CAG|
|R|L|S|I|S|R|D|T|S|K|S|Q|

| | | | | | | | | | | | |
|---|---|---|---|---|---|---|---|---|---|---|---|
|GTT|TTC|TTA|AAG|ATG|AAC|AGT|CTG|CAA|AGT|GAA|GAC|
|V|F|L|K|M|N|S|L|Q|S|E|D|

| | | | | | | | | | | | |
|---|---|---|---|---|---|---|---|---|---|---|---|
|ACA|GCC|ATG|TAC|TTC|TGT|GCC|AGA|GAG|TAC|TAC|GGC|
|T|A|M|Y|F|C>|A|R|E|Y|Y|G|

| | | | | | | | | | | | |
|---|---|---|---|---|---|---|---|---|---|---|---|
|TAC|TTT|GAT|TAC|TGG|GGC|CAA|GGA|GTC|ATG|GTC|ACA|
|Y|F|D|Y|W|G|Q|G|V|M|V|T|

| | | | | |
|---|---|---|---|---|
|GTC|TCC|TCA| SEQ ID NO:5 | |
|V|S|S>| SEQ ID NO:6 | |

FIG.2

| | | | | | | | | | | | |
|---|---|---|---|---|---|---|---|---|---|---|---|
| ATG | GCT | GTG | CCC | ACT | CAG | CTC | CTG | GGG | TTG | TTG | TTG |
| M | A | V | P | T | Q | L | L | G | L | L | L |
| CTG | TGG | ATT | ACA | GAT | GCC | ATA | TGT | GAC | ATC | CAG | ATG |
| L | W | I> | T | D | A | I | C | D | I | Q | M |
| ACA | CAG | TCT | CCA | GCT | TCC | CTG | TCT | GCA | TCT | CTG | GGA |
| T | Q | S | P | A | S> | L | S | A | S | L | G |
| GAA | ACT | ATC | TCC | ATC | GAA | TGT | CTA | GCA | AGT | GAG | GGC |
| E | T | I | S | I | E | C | L | A> | S | E | G |
| ATT | TCC | AGT | TAT | TTA | GCG | TGG | TAT | CAG | CAG | AAG | CCA |
| I | S | S | Y | L | A | W | Y | Q | Q | K | P> |
| GGG | AAA | TCT | CCT | CAG | CTC | CTG | ATC | TAT | GGT | GCA | AAT |
| G | K | S | P | Q | L | L | I | Y | G | A | N |
| AGC | TTG | CAA | ACT | GGG | GTC | CCA | TCA | CGG | TTC | AGT | GGC |
| S | L | Q> | T | G | V | P | S | R | F | S | G |
| AGT | GGA | TCT | GCC | ACA | CAA | TAT | TCT | CTC | AAG | ATC | AGC |
| S | G | S | A | T | Q | Y | S | L | K | I | S |
| AGC | ATG | CAA | CCT | GAA | GAT | GAA | GGG | GAT | TAT | TTC | TGT |
| S | M | Q | P | E | D | E | G | D> | Y | F | C |
| CAA | CAG | AGT | TAC | AAG | TTT | CCG | AAC | ACG | TTT | GGA | GCT |
| Q | Q | S | Y | K | F | P | N | T | F | G | A> |
| GGG | ACC | AAG | CTG | GAA | CTG | AAA | CGG | | SEQ | ID | NO:7 |
| G | T | K | L | E | L | K | R> | | SEQ | ID | NO:8 |

FIG.3

Framework 1

```
                     1 1112 2
              9      5 7890 2
hu gpl   DIQMTQSPSSLSASVGDRVTITC  SEQ ID NO:9
39D10    DIQMTQSPASLSASLGETISIEC  SEQ ID NO:10
```

Framework 2

```
            4 4
            3 5
hu gpl   WYQQKPGKAPKLLIY  SEQ ID NO:11
39D10    WYQQKPGKSPQLLIY  SEQ ID NO:12
```

Framework 3

```
              6 777 7   7      888 8
              8 012 4   8      345 7
hu gpl   GVPSRFSGSGSGTDFTLTISSLQPEDFATYYC
         SEQ ID NO:13
39D10    GVPSRFSGSGSATQYSLKISSMQPEDEGDYFC
         SEQ ID NO:14
```

Framework 4

```
           1  1 1
           0  0 0
           0  4 6
hu gpl   FGQGTKVEIKR  SEQ ID NO:15
39D10    FGAGTKLELKR  SEQ ID NO:16
```

FIG.4

Framework 1

```
            111 1 2 22  2223
            567 9 1 34  7890
hu gp3   EVQLVESGGGLVQPGGSLRLSCAASGFTFS
         SEQ ID NO:17
39D10    ?????ESGGGLVQPSQTLSLTCTVSGLSLT
         SEQ ID NO:18
```

Framework 2

```
          3   4      44
          7   0      89
hu gp3   WVRQAPGKGLEWVS SEQ ID NO:19
39D10    WIRQPPGKGLEWMG SEQ ID NO:20
```

Framework 3

```
          66   7  7777 8    88     8 9
          78   3  6789 1    34     9 1
hu gp3   RFTISRDNSKNTLYLQMNSLRAEDTAVYYCAR
         SEQ ID NO:21
39D10    RLSISRDTSKSQVFLKMNSLQSEDTAMYFCAR
         SEQ ID NO:22
```

Framework 4

```
           11
           00
           78
hu gp3   WGQGTLVTVSS SEQ ID NO:23
39D10    WGQGVMVTVSS SEQ ID NO:24
```

FIG.5

| | | | | | | | | | |
|---|---|---|---|---|---|---|---|---|---|
| TTCGAAGCCGCCACC | ATG | TCT | GTC | CCC | ACC | CAA | GTC | CTC | |
| | M | S | V | P | T | Q | V | L | |

```
TTCGAAGCCGCCACC ATG TCT GTC CCC ACC CAA GTC CTC
                 M   S   V   P   T   Q   V   L

GGT CTC CTG CTG CTG TGG CTT ACA GAT GCC AGA TGT
 G   L   L>  L   L   W   L   T   D   A   R   C

GAC ATT CAA ATG ACC CAG AGC CCA TCC AGC CTG AGC
 D   I   Q   M   T   Q>  S   P   S   S   L   S

GCA TCT GTA GGA GAC CGG GTC ACC ATC ACA TGT CTA
 A   S   V   G   D   R   V   T   I>  T   C   L

GCA AGT GAG GGC ATC TCC AGT TAC TTA GCG TGG TAC
 A   S   E   G   I   S   S   Y   L   A   W   Y>

CAG CAG AAG CCC GGG AAA GCT CCT AAG CTC CTG ATC
 Q   Q   K   P   G   K   A   P   K   L   L   I

TAT GGT GCG AAT AGC TTG CAG ACT GGA GTA CCA TCA
 Y   G   A>  N   S   L   Q   T   G   V   P   S

AGA TTC AGT GGC TCA GGA TCC GCT ACA GAC TAC ACG
 R   F   S   G   S   G>  S   A   T   D   Y   T

CTC ACG ATC TCC AGC CTA CAG CCT GAA GAT TTC GCA
 L   T   I   S   S   L   Q   P   E>  D   F   A

ACG TAT TAC TGT CAA CAG TCG TAT AAG TTC CCG AAC
 T   Y   Y   C   Q   Q   S   Y   K   F   P   N>

ACA TTC GGT CAA GGC ACC AAG GTC GAA GTC AAA CGT
 T   F   G   Q   G   T   K   V   E   V   K   R>
```

SEQ ID NO:25
SEQ ID NO:26

FIG.6

```
AAGCTTGCCGCCACC ATG GGC TGG AGC TGT ATC ATC CTC
                M   G   W   S   C   I   I   L

TTC TTA GTA GCA ACA GCT ACA GGT GTC CAC TCC GAG
F   L   V>  A   T   A   T   G   V   H   S   E

GTC CAA CTG GTA GAA TCT GGA GGT GGT CTC GTA CAG
V   Q   L   V   E   S>  G   G   G   L   V   Q

CCA GGA GGA TCT CTG CGA CTG AGT TGC GCC GTC TCT
P   G   G   S   L   R   L   S   C>  A   V   S

GGG TTA TCA TTA ACT AGT AAT AGT GTG AAC TGG ATA
G   L   S   L   T   S   N   S   V   N   W   I>

CGG CAA GCA CCT GGC AAG GGT CTC GAG TGG GTT GGA
R   Q   A   P   G   K   G   L   E   W   V   G

CTA ATA TGG AGT AAT GGA GAC ACA GAT TAT AAT TCA
L   I   W>  S   N   G   D   T   D   Y   N   S

GCT ATC AAA TCT CGA TTC ACA ATC TCT AGA GAC ACT
A   I   K   S   R   F>  T   I   S   R   D   T

TCG AAG AGC ACC GTA TAC CTG CAG ATG AAC AGT CTG
S   K   S   T   V   Y   L   Q   M>  N   S   L

AGA GCT GAA GAT ACT GCA GTC TAC TAC TGT GCT CGT
R   A   E   D   T   A   V   Y   Y   C   A   R>

GAG TAC TAT GGA TAT TTC GAC TAT TGG GGT CAA GGT
E   Y   Y   G   Y   F   D   Y   W   G   Q   G

ACC CTA GTC ACA GTC TCC TCA    SEQ ID NO:27
T   L   V>  T   V   S   S>     SEQ ID NO:28
```

FIG.9

| Antibody | kd $(\times 10^{-10} M)$ | kass $(\times 10^5 M^{-1} sec^{-1})$ |
|---|---|---|
| Chimeric 39D10 | 1.14 | 5.77 |
| | 0.63 | 6.27 |
| CTIL-5-10gH/gL6 | 0.89 | 4.55 |
| | 1.18 | 4.72 |

SEQUENCE LISTING

```
<160> NUMBER OF SEQ ID NOS:   28

<210> SEQ ID NO 1
<211> LENGTH: 47
<212> TYPE: DNA
<213> ORGANISM: Artificial Sequence
<220> FEATURE:
<221> NAME/KEY: misc_feature
<223> OTHER INFORMATION: Primer

<400> SEQUENCE: 1
gcgcgcaagc ttgccgccac catgaagwtg tggttaaact gggtttt              47

<210> SEQ ID NO 2
<211> LENGTH: 37
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
gcagatgggc ccttcgttga ggctgmrgag acdgtga                         37

<210> SEQ ID NO 3
<211> LENGTH: 44
<212> TYPE: DNA
<213> ORGANISM: Artificial Sequence
<220> FEATURE:
<221> NAME/KEY: misc_feature
<223> OTHER INFORMATION: Primer

<400> SEQUENCE: 3
ggactgttcg aagccgccac catgagtgtg ctcactcagg tcct                 44

<210> SEQ ID NO 4
<211> LENGTH: 30
<212> TYPE: DNA
<213> ORGANISM: Artificial Sequence
<220> FEATURE:
<221> NAME/KEY: misc_feature
<223> OTHER INFORMATION: Primer

<400> SEQUENCE: 4
ggatacagtt ggtgcagcat ccgtacgttt                                 30

<210> SEQ ID NO 5
```

```
<211> LENGTH: 333
<212> TYPE: DNA
<213> ORGANISM: Rattus rattus

<400> SEQUENCE: 5
gaatctggag gaggcttggt acagccatca cagaccctgt ctctcacctg cactgtctct      60
gggttatcat taaccagcaa tagtgtgaac tggattcggc agcctccagg aaagggtctg     120
gagtggatgg gactaatatg gagtaatgga gacacagatt ataattcagc tatcaaatcc     180
cgactgagca tcagtaggga cacctcgaag agccaggttt tcttaaagat gaacagtctg     240
caaagtgaag acacagccat gtacttctgt gccagagagt actacggcta ctttgattac     300
tggggccaag gagtcatggt cacagtctcc tca                                  333

<210> SEQ ID NO 6
<211> LENGTH: 111
<212> TYPE: PRT
<213> ORGANISM: Rattus rattus

<400> SEQUENCE: 6

Glu Ser Gly Gly Gly Leu Val Gln Pro Ser Gln Thr Leu Ser Leu Thr
 1               5                  10                  15

Cys Thr Val Ser Gly Leu Ser Thr Ser Asn Ser Val Asn Trp Ile
                20                  25                  30

Arg Gln Pro Pro Gly Lys Gly Leu Glu Trp Met Gly Leu Ile Trp Ser
            35                  40                  45

Asn Gly Asp Thr Asp Tyr Asn Ser Ala Ile Lys Ser Arg Leu Ser Ile
        50                  55                  60

Ser Arg Asp Thr Ser Lys Ser Gln Val Phe Leu Lys Met Asn Ser Leu
65                  70                  75                  80

Gln Ser Glu Asp Thr Ala Met Tyr Phe Cys Ala Arg Glu Tyr Tyr Gly
                85                  90                  95

Tyr Phe Asp Tyr Trp Gly Gln Gly Val Met Val Thr Val Ser Ser
            100                 105                 110

<210> SEQ ID NO 7
<211> LENGTH: 384
<212> TYPE: DNA
<213> ORGANISM: Rattus rattus

<400> SEQUENCE: 7
atggctgtgc ccactcagct cctggggttg ttgttgctgt ggattacaga tgccatatgt      60
gacatccaga tgacacagtc tccagcttcc ctgtctgcat ctctgggaga aactatctcc     120
atcgaatgtc tagcaagtga gggcatttcc agttatttag cgtggtatca gcagaagcca     180
gggaaatctc ctcagctcct gatctatggt gcaaatagct tgcaaactgg ggtcccatca     240
cggttcagtg gcagtggatc tgccacacaa tattctctca agatcagcag catgcaacct     300
gaagatgaag gggattattt ctgtcaacag agttacaagt ttccgaacac gtttggagct     360
gggaccaagc tggaactgaa acgg                                            384

<210> SEQ ID NO 8
<211> LENGTH: 128
<212> TYPE: PRT
<213> ORGANISM: Rattus rattus

<400> SEQUENCE: 8

Met Ala Val Pro Thr Gln Leu Leu Gly Leu Leu Leu Leu Trp Ile Thr
 1               5                  10                  15
```

```
Asp Ala Ile Cys Asp Ile Gln Met Thr Gln Ser Pro Ala Ser Leu Ser
            20                  25                  30

Ala Ser Leu Gly Glu Thr Ile Ser Ile Glu Cys Leu Ala Ser Glu Gly
        35                  40                  45

Ile Ser Ser Tyr Leu Ala Trp Tyr Gln Gln Lys Pro Gly Lys Ser Pro
    50                  55                  60

Gln Leu Leu Ile Tyr Gly Ala Asn Ser Leu Gln Thr Gly Val Pro Ser
65                  70                  75                  80

Arg Phe Ser Gly Ser Gly Ser Ala Thr Gln Tyr Ser Leu Lys Ile Ser
                85                  90                  95

Ser Met Gln Pro Glu Asp Glu Gly Asp Tyr Phe Cys Gln Gln Ser Tyr
            100                 105                 110

Lys Phe Pro Asn Thr Phe Gly Ala Gly Thr Lys Leu Glu Leu Lys Arg
            115                 120                 125

<210> SEQ ID NO 9
<211> LENGTH: 23
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 10
<211> LENGTH: 23
<212> TYPE: PRT
<213> ORGANISM: Rattus rattus

<400> SEQUENCE: 10

Asp Ile Gln Met Thr Gln Ser Pro Ala Ser Leu Ser Ala Ser Leu Gly
1               5                   10                  15

Glu Thr Ile Ser Ile Glu Cys
            20

<210> SEQ ID NO 11
<211> LENGTH: 15
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 11

Trp Tyr Gln Gln Lys Pro Gly Lys Ala Pro Lys Leu Leu Ile Tyr
1               5                   10                  15

<210> SEQ ID NO 12
<211> LENGTH: 15
<212> TYPE: PRT
<213> ORGANISM: Rattus rattus

<400> SEQUENCE: 12

Trp Tyr Gln Gln Lys Pro Gly Lys Ser Pro Gln Leu Leu Ile Tyr
1               5                   10                  15
```

```
<210> SEQ ID NO 13
<211> LENGTH: 32
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 32
<212> TYPE: PRT
<213> ORGANISM: Rattus rattus

<400> SEQUENCE: 14

Gly Val Pro Ser Arg Phe Ser Gly Ser Gly Ser Ala Thr Gln Tyr Ser
1               5                   10                  15

Leu Lys Ile Ser Ser Met Gln Pro Glu Asp Glu Gly Asp Tyr Phe Cys
            20                  25                  30

<210> SEQ ID NO 15
<211> LENGTH: 11
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 15

Phe Gly Gln Gly Thr Lys Val Glu Ile Lys Arg
1               5                   10

<210> SEQ ID NO 16
<211> LENGTH: 11
<212> TYPE: PRT
<213> ORGANISM: Rattus rattus

<400> SEQUENCE: 16

Phe Gly Ala Gly Thr Lys Leu Glu Leu Lys Arg
1               5                   10

<210> SEQ ID NO 17
<211> LENGTH: 30
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 18
<211> LENGTH: 30
<212> TYPE: PRT
<213> ORGANISM: Rattus rattus
<220> FEATURE:
<221> NAME/KEY: UNSURE
```

```
<222> LOCATION: (1)..(5)
<223> OTHER INFORMATION: Xaa is Unknown

<400> SEQUENCE: 18

Xaa Xaa Xaa Xaa Xaa Glu Ser Gly Gly Gly Leu Val Gln Pro Ser Gln
1               5                   10                  15

Thr Leu Ser Leu Thr Cys Thr Val Ser Gly Leu Ser Leu Thr
            20                  25                  30

<210> SEQ ID NO 19
<211> LENGTH: 14
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 19

Trp Val Arg Gln Ala Pro Gly Lys Gly Leu Glu Trp Val Ser
1               5                   10

<210> SEQ ID NO 20
<211> LENGTH: 14
<212> TYPE: PRT
<213> ORGANISM: Rattus rattus

<400> SEQUENCE: 20

Trp Ile Arg Gln Pro Pro Gly Lys Gly Leu Glu Trp Met Gly
1               5                   10

<210> SEQ ID NO 21
<211> LENGTH: 32
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 21

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 22
<211> LENGTH: 32
<212> TYPE: PRT
<213> ORGANISM: Rattus rattus

<400> SEQUENCE: 22

Arg Leu Ser Ile Ser Arg Asp Thr Ser Lys Ser Gln Val Phe Leu Lys
1               5                   10                  15

Met Asn Ser Leu Gln Ser Glu Asp Thr Ala Met Tyr Phe Cys Ala Arg
            20                  25                  30

<210> SEQ ID NO 23
<211> LENGTH: 11
<212> TYPE: PRT
<213> ORGANISM: Artificial Sequence
<220> FEATURE:
<221> NAME/KEY: misc_feature
<223> OTHER INFORMATION: Consensus

<400> SEQUENCE: 23

Trp Gly Gln Gly Thr Leu Val Thr Val Ser Ser
```

```
1               5                    10
```

<210> SEQ ID NO 24
<211> LENGTH: 11
<212> TYPE: PRT
<213> ORGANISM: Rattus rattus

<400> SEQUENCE: 24

```
Trp Gly Gln Gly Val Met Val Thr Val Ser Ser
1               5                   10
```

<210> SEQ ID NO 25
<211> LENGTH: 399
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 25

```
ttcgaagccg ccaccatgtc tgtccccacc caagtcctcg gtctcctgct gctgtggctt      60
acagatgcca gatgtgacat tcaaatgacc cagagcccat ccagcctgag cgcatctgta    120
ggagaccggg tcaccatcac atgtctagca agtgagggca tctccagtta cttagcgtgg    180
taccagcaga agcccgggaa agctcctaag ctcctgatct atggtgcgaa tagcttgcag    240
actggagtac catcaagatt cagtggctca ggatccgcta cagactacac gctcacgatc    300
tccagcctac agcctgaaga tttcgcaacg tattactgtc aacagtcgta taagttcccg    360
aacacattcg gtcaaggcac caaggtcgaa gtcaaacgt                           399
```

<210> SEQ ID NO 26
<211> LENGTH: 128
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 26

```
Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
                20                  25                  30

Ala Ser Val Gly Asp Arg Val Thr Ile Thr Cys Leu Ala Ser Glu Gly
            35                  40                  45

Ile Ser Ser Tyr Leu Ala Trp Tyr Gln Gln Lys Pro Gly Lys Ala Pro
        50                  55                  60

Lys Leu Leu Ile Tyr Gly Ala Asn Ser Leu Gln Thr Gly Val Pro Ser
65                  70                  75                  80

Arg Phe Ser Gly Ser Gly Ser Ala Thr Asp Tyr Thr Leu Thr Ile Ser
                85                  90                  95

Ser Leu Gln Pro Glu Asp Phe Ala Thr Tyr Tyr Cys Gln Gln Ser Tyr
            100                 105                 110

Lys Phe Pro Asn Thr Phe Gly Gln Gly Thr Lys Val Glu Val Lys Arg
        115                 120                 125
```

<210> SEQ ID NO 27
<211> LENGTH: 420
<212> TYPE: DNA
<213> ORGANISM: Artificial Sequence
<220> FEATURE:

-continued

```
<221> NAME/KEY: misc_feature
<223> OTHER INFORMATION: Novel Sequence

<400> SEQUENCE: 27
aagcttgccg ccaccatggg ctggagctgt atcatcctct tcttagtagc aacagctaca      60
ggtgtccact ccgaggtcca actggtagaa tctggaggtg gtctcgtaca gccaggagga     120
tctctgcgac tgagttgcgc cgtctctggg ttatcattaa ctagtaatag tgtgaactgg     180
atacggcaag cacctggcaa gggtctcgag tgggttggac taatatggag taatggagac     240
acagattata attcagctat caaatctcga ttcacaatct ctagagacac ttcgaagagc     300
accgtatacc tgcagatgaa cagtctgaga gctgaagata ctgcagtcta ctactgtgct     360
cgtgagtact atggatattt cgactattgg ggtcaaggta ccctagtcac agtctcctca     420

<210> SEQ ID NO 28
<211> LENGTH: 135
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 28

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Val Ser Gly Leu Ser Leu
        35                  40                  45

Thr Ser Asn Ser Val Asn Trp Ile Arg Gln Ala Pro Gly Lys Gly Leu
    50                  55                  60

Glu Trp Val Gly Leu Ile Trp Ser Asn Gly Asp Thr Asp Tyr Asn Ser
65                  70                  75                  80

Ala Ile Lys Ser Arg Phe Thr Ile Ser Arg Asp Thr Ser Lys Ser Thr
                85                  90                  95

Val Tyr Leu Gln Met Asn Ser Leu Arg Ala Glu Asp Thr Ala Val Tyr
            100                 105                 110

Tyr Cys Ala Arg Glu Tyr Tyr Gly Tyr Phe Asp Tyr Trp Gly Gln Gly
        115                 120                 125

Thr Leu Val Thr Val Ser Ser
    130                 135
```

NUCLEIC ACIDS ENCODING INTERLEUKIN-5 SPECIFIC RECOMBINANT ANTIBODIES

This Application is a continuation of Application Ser. No. 08/470,139, filed Jun. 6, 1995, now U.S. Pat. No. 5,998,586.

The present invention relates to a recombinant antibody molecule (RAM), and especially a humanized antibody molecule (HAM) having specificity for human interleukin-5 (hIL-5), the nucleic acids which encode the heavy and light chain variable domains of said recombinant antibody, a process for producing said antibody using recombinant DNA technology and the therapeutic use of the recombinant antibody.

In the present application, the term "recombinant antibody molecule" (RAM) is used to describe an antibody produced by a process involving the use of recombinant DNA technology. The term "humanized antibody molecule" (HAM) is used to describe a molecule being derived from a human immunoglobulin. The antigen binding site may comprise either complete variable domains fused onto constant domains or one of more complementary determining regions (CDRs) grafted onto appropriate framework regions in the variable domain. The abbreviation "MAb" is used to indicate a monoclonal antibody.

The term "recombinant antibody molecule" includes not only complete immunoglobulin molecules but also any antigen binding immunoglobulin fragments, such as Fv, Fab and F(ab')$_2$ fragments, and any derivatives thereof, such as single chain Fv fragments.

Natural immunoglobulins have been used in assay, diagnosis and, to a limited extent, therapy. The use of immunoglobulins in therapy has been hindered as most antibodies of potential use as therapeutic agents are MAbs produced by fusions of a rodent spleen cells with rodent myelcma cells. These Mbs are therefore essentially rodent proteins. The use of these MAbs as therapeutic agents in human can give rise to an undesirable immune response termed the HAMA (Human Anti-mouse Antibody) response. The use of rodent MAbs as therapeutic agents in humans is inherently limited by the fact that the human subject will mount an immunological response to the NAb which would either remove it entirely or at least reduce its effectiveness.

A number of techniques to reduce the antigenic characteristics of such non-human MAbs have been developed. These techniques generally involve the use of recombinant DNA technology to manipulate DNA sequences encoding the polypeptide chains of the antibody molecule. These methods are generally termed "humanization" techniques.

Early methods for humanizing MAbs Involved the production of chimeric antibodies in which an antigen binding site comprising the complete variable domains of one antibody are fused to constant domains derived from another antibody. Methods for carrying out such chimerisation procedures are described in EP 0120694 (Celltech Limited) and EP 0125023 (Genentech Inc. and City of Hope). Humanized chimeric antibodies, however, still contain a significant portion of non-human amino acid sequences, and can still elicit some HAMA response, particularly if administered over a prolonged period [Begent et al., Br. J. Cancer, 62, 487 (1990)].

An alternative approach, described in EP-A-0239400 (Winter), involves the grafting of the complementarity determining region (CDRs) of a mouse MAb on to framework regions of the variable domains of a human immunoglobulin using recombinant DNA techniques. There are three CDRs (CDR1, CDR2 and CDR3) in each of the heavy and light chain variable domains. Such CDR-grafted humanized antibodies are much less likely to give rise to a HAMA response than humanized chimeric antibodies in view of the much lower proportion of non-human amino acid sequences which they contain. In Riechmann et al. [Nature, 332 323–324 (1988)] it was found that the transfer of the CDRs alone, as defined by Kabat [Sequences or Proteins of Immunological Interest, US Department of Health and Human Services, NIH, USA (1987)], was not sufficient to provide satisfactory antigen binding activity in the CDR-grafted product. Riechmann et al. found that it was necessary to convert a number of residues outside the CORs, in particular in the loop adjacent CDR1. However, the binding affinity of the best CDR-grafted antibodies obtained was still significantly less than that of the original MAb.

In WO 91/09967, Adair et al. described CDR-grafted antibody heavy and light chains, and determined a hierarchy of donor residues.

In WO 93/16194, Chou et al. described the design, cloning and expression of humanized monoclonal antibodies against human interleukin-5. A method for selecting human antibody sequences to be used as human frameworks for humanization of an animal antibody is suggested, comprising the steps of comparing human variable domain sequences with the variable domain sequences of the animal MAb that is to be humanized for percentage identities, sequence ambiguities and similar PIN-region spacing. PIN-region spacing is defined as the number of residues between the cysteine residues forming the intra domain disulfide bridges. The human antibody having the best combination of these features is selected. A method for determining which variable domain residues of an animal MAb which should be selected for humanization is also suggested, comprising determining potential minimum residues (residues which comprise CDR structural loops and the residues required to support and/or orientate the CDR structural loops) and maximum residues (residues which comprise Kabat CDRs, CDR structural loops, residues required to support and/or orientate the CDR structural loops and residues which fall within about 10 Å of a CDR structural loop and possess a water solvent accessible surface of about 5 Å$^2$ or greater) of the animal monoclonal antibody. Furthermore, computer modelling is performed on all possible recombinant antibodies, comprising the human antibody framework sequence into which minimum and maximum residues have been inserted. The minimum or maximum residues are selected based on the combination which produces a recombinant antibody having a computer-model structure closest to that of the animal monoclonal antibody. The humanized anti-IL-5 antibody obtained appears to have lost a substantial amount of its affinity for the hIL-5 molecule.

It is an aim of the present invention to provide a humanized antibody molecule having improved affinity for the hIL-5 molecule.

Accordingly the present invention provides a RAM having affinity for human IL-5 and comprising antigen binding regions derived from heavy and/or light chain variable domains of a donor antibody having affinity for human IL-5, the RAM having a binding affinity similar to that of the donor antibody.

The RAM of invention may comprise antigen binding regions from any suitable donor anti-IL-5 antibody. Typically the donor anti-IL-5 antibody is a rodent MAb. Preferably the donor antibody is MAb 39D10.

The variable domains of the heavy and light chains of MAb 39D10 are hereinafter specifically described with reference to FIGS. 1 and 2.

According to one preferred aspect of the invention, the RAM of the present invention is an anti-IL-5 antibody molecule having affinity for the human IL-5 antigen comprising a composite heavy chain and a complementary light chain, said composite heavy chain having a variable domain comprising predominantly acceptor antibody heavy chain framework residues and donor antibody heavy chain antigen-binding residues, said donor antibody having affinity for human IL-5, wherein said composite heavy chain comprises donor residues at least at positions 31–35, 50–65 and 95–102 (according to the Kabat numbering system) [Kabat et al., Sequences of Proteins of Immunological Interest, Vol I, Fifth Edition, 1991, US Department of Health and Human Services, National Institute of Health].

Preferably, the composite heavy chain framework additionally comprises donor residues at positions 23, 24, 27–30, 37, 49, 73 and 76–76 or 24, 27–30, 37, 49, 73, 76 and 78.

According to a second preferred aspect of the present invention, there is provided an anti-IL-5 antibody molecule having affinity for a human IL-5 antigen comprising a composite light chain and a complementary heavy chain, said composite light chain having a variable domain comprising predominantly acceptor antibody light chain framework residues and donor antibody light chain antigen-binding residues, said donor antibody having affinity for human IL-5, wherein said composite light chain comprises donor residues at least at positions 24–34, 50–56 and 89–97 (according to the Kabat numbering system).

Preferably, the composite light chain framework additionally comprises donor residues at positrons 22, 68 and 71 or at positions 68 and 71.

According to a third preferred aspect of the present invention, there is provided an anti-IL-5 antibody molecule having affinity for a human IL-5 antigen comprising a composite heavy chain according to the first aspect of the invention and a composite light chain according to the second aspect of the invention.

Preferably, each RAM of the invention has an affinity constant for human IL-5 of greater than $10^{-9}$M.

It will be appreciated that the invention is widely applicable to the production of anti-IL-5 RAMs in general. Thus, the donor antibody may be any anti-IL-5 antibody derived from any animal. The acceptor antibody may be derived from an animal of the same species and may even be of the same antibody class or sub-class. More usually, however, the donor and acceptor antibodies are derived from animals from different species Typically, the donor anti-IL-5 antibody is a non-human antibody, such as d rodent MAb, and the acceptor antibody is a human antibody.

Any appropriate acceptor variable framework sequence may be used having regard to class or type of the donor antibody from which the antigen binding regions are derived. Preferably, the type of acceptor framework used is of the same or similar class or type as that of the donor antibody. Conveniently, the framework chosen has the most homology to the donor antibody. Preferably, the human group III gamma germ line frameworks are used for the composite heavy chain and the human group I kappa germ line frameworks are used for the composite light chains.

The constant region domains of the RAMs of the invention may be selected having regard to the proposed functions of the antibody, in particular the effector functions which may be required. For example, the constant region domains may be human IgA, IgE, IgG or IgM domains. In particular, IgG human constant region domains may be used, especially of the IgG1 and the IgG3 isotype, when the humanized antibody molecule is intended for therapeutic uses, and antibody effector functions are required. Alternatively, IgG2 and IgG4 isotypes may be used where the humanized antibody molecule is intended for therapeutic purposes and antibody effector functions are not required, e.g. for specifically binding to and neutralizing the biological activity of human IL-5. Modified human constant region domains may also be used in which one or more amino acid residues have been altered or deleted to change a particular effector function. Preferably, the constant region domains of the RAMs are human IgG4.

The residue designations given above and elsewhere in the present application are numbered according to the Kabat numbering [Kabat et al., Sequences of Proteins of immunological Interest, Vol T, Fifth Edition, 1991, U.S. Department of Health and Human Services, National Institute of Health]. Thus, the residue designations do not always correspond directly with a linear numbering of the amino acid residues. The actual linear amino acid sequence may contain fewer or additional amino acids than in the Kabat numbering, corresponding to a shortening of, or insertion into, the basic variable domain structure.

Also the anti-IL-5 antibody molecules of the present invention may have attached to them effector or reporter molecules. Alternatively, the procedures of recombinant DNA technology may be used to produce immunoglobulin molecules in which the Fc fragment or CH3 domain of a complete immunoglobulin has been replaced by, or has been attached thereto by peptide linkage, a functional non-immunoglobulin protein, such as an enzyme, cytokine, growth factor or toxin molecule.

Thus, the remainder of the antibody molecules need not comprise only sequences from immunoglobulins. For instance, a gene may be constructed in which a DNA sequence encoding part of a human immunoglobulin chain is fused to a DNA sequence encoding the amino acid sequence of a polypeptide effector or reporter molecule.

Further aspects of the invention include DNA sequences coding for the composite heavy chain and the composite light chain. The cloning and expression vectors containing the DNA sequences, host cells transformed with the DNA sequences and the processes for producing the antibody molecules comprising expressing the DNA sequences in the transformed host cells are also further aspects of the invention.

The general methods by which vectors may be constructed, transfection methods and culture methods are well known in the art and form no part of the invention.

The DIVA sequences which encode the anti-IL-5 donor amino acid sequences may be obtained by methods well known in the art (see, for example, International Patent Application No. WO 93/16184). For example, the anti-IL-5 coding sequences may be obtained by genomic cloning or cDNA cloning from suitable hybridoma cell lines, e.g. the 39D10 cell line. Positive clones may be screened using appropriate probes for the heavy and light chains required. Also PCR cloning may be used.

The DNA coding for acceptor amino acid sequences may be obtained in any appropriate way. For example, DNA sequences coding for preferred human acceptor frameworks such as human group I light chains and human group III heavy chains, are widely available to workers in the art.

The standard techniques of molecular biology may be used to prepare the desired DNA sequences. The sequences may be synthesised completely or in part using oligonucleotide synthesis techniques. Site-directed mutagenesis and polymerase chain reaction (PCR) techniques may be used as appropriate. For example, oligonucleotide directed synthesis as described by Jones et al, [Nature, 321, 522 (1986)] may be used. Also oligonucleotide directed mutagenesis of a pre-existing variable region as, for example, described by Verhoeyen et al. [Science, 239, 1534–1536 (1988)] may be used. Also enzymatic filling in of gapped oligonucleotides using T4 DNA polymerase as, for example, described by Queen et al. [Proc. Natl. Acad. Sci. USA, 6, 10029–10033 (1989) and WO 90/07861] may be used.

Any suitable host cell and vector system may be used for the expression of DNA sequences coding for the RAM. Preferably, eucaryotic, e.g. mammalian, host cell expression systems are used. In particular, suitable mammalian host cells include CHO cells and myeloma or hybridoma cell lines.

Thus, according to a further aspect of the present invention a process for producing an anti-IL-5 RAM is provided comprising:

(a) producing in a first expression vector a first operon having a DNA sequence which encodes a composite heavy chain, as defined according to the first preferred aspect of the invention;

(b) optionally producing in the first or a second expression vector a second operon having a DNA sequence which encodes a complementary light chain, which may be a composite light chain as defined according to the second preferred aspect of the invention;

(c) transfecting a host cell with the or each vector; and (d) culturing a transtected cell line to produce the RAM.

Alternatively, the process may involve the use of sequences encoding a composite light chain and a complementary heavy chain.

For the production of RAMs comprising both heavy and light chains, the cell lines may be transfected with two vectors. The first vector may contain an operon encoding a composite or complementary heavy chain and the second vector may contain an operon encoding a complementary or composite light chain. Preferably, the vectors are identical except insofar as the coding sequences and selectable markers ore concerned so as to ensure as far as possible that each polypeptide chain is equally expressed. In a preferred alternative, a single vector may be used, the vector including the sequences encoding both the heavy chain and the light chain.

The DNA in the coding sequences for the heavy and light chains may comprise cDNA or genomic DNA or both.

The present invention also includes therapeutic and diagnostic compositions comprising the RAMs and uses of such compositions in therapy and diagnosis.

Accordingly, in a further aspect the invention provides a therapeutic or diagnostic composition comprising a RAM according to previous aspects of the invention in combination with a pharmaceutically acceptable excipient, diluent or carrier.

These compositions can be prepared using the RAMs of the present invention, for instance as whole antibodies, single chain Fv fragments or antibody fragments, such as Fab or Fv fragments. Such compositions have IL-5 blocking or antagonistic effects and can be used to suppress IL-5 activity.

The compositions according to the invention may be formulated in accordance with conventional practice for administration by any suitable route, and may generally be in a liquid form [e.g. a solution of the RAM in a sterile physiologically acceptable buffer] for administration by for example an intravenous, intraperitoneal or intramuscular route; in spray form, for example for administration by a nasal or buccal route; or in a form suitable for implantation.

The invention also provides a method of therapy or diagnosis comprising administering an effective amount, preferably 0.1 to 10 mg/kg body weight, of a RAM according to previous aspects of the invention to a human or animal subject. The exact dosage and total dose will vary according to the intended use of the RAM and an the age and condition of the patient to be treated. The RAM may be administered as a single dose, or in a continuous manner over a period of time. Doses may be repeated as appropriate.

The RAM according to previous aspects of the invention may be used for any of the therapeutic uses for which anti-IL-5 antibodies, e.g. D9D10 have been used or may be used in the future.

IL-5 is a primary activator of eosinophils, and blocking the function of this cytokine with antibodies has been shown to prevent or reduce eosinophilia which is associated with certain allergic diseases. Thus the RAM according to the invention may be used for this purpose, and in particular may be of use in the treatment of asthma, where it may be expected to prevent the accumulation and activation of eosinophils in asthmatic lungs, thereby reducing bronchial inflammation and airway narrowing. For use in the treatment of asthma the RAM according to the invention may advantageously be a single chain Fv fragment, formulated as a spray, for administration for example via the nasal route.

A preferred protocol for obtaining an anti-IL-5 antibody molecule in accordance with the present invention is set out below. This protocol is given without prejudice to the generality of the invention as hereinbefore described and defined.

The 39D10 rat monoclonal antibody raised against human IL-5 is used as the donor antibody. The variable domains of the heavy and light chains of 39D10 have previously been cloned (WO 93/16184) and the nucleotide and predicted amino acid sequences of these domains are shown in FIGS. 1 and 2. The appropriate acceptor heavy and light chain variable domains must be determined and the amino acid sequence known. The RAM is then designed starting from the basis of the acceptor sequence.

1. The CDRs

At a first step, donor residues are substituted for acceptor residues In the CDRs. For this purpose, the CDRs are preferably defined as follows:

heavy chain:
   CDR1; residues 31–35
   CDR2: residues 50–65
   CDR3: residues 95–102
light chain:
   CDR1: residues 24–34
   CDR2: residues 50 to 56
   CDR3: residues 89 to 97

The positions at which donor residues are to be substituted for acceptor residues in the framework are then chosen as follows, first of all with respect to the heavy chain and subsequently with respect to the light chain.

2. Heavy Chain 2.1 Donor residues are used either at all of positions 24, 27 to 30, 37, 49, 73, 76 and 78 or at all of positions 23, 24, 27 to 30, 37, 49, 73 and 76 to 78 of the heavy chain.

3. Light Chain 3.1 Donor residues are used either at all of positions 22, 68 and 71 or at all of positions 68 and 71.

The present invention relates to a recombinant anti-IL-5 antibody molecule having a binding affinity substantially equal to that of the donor antibody. The present invention is now described, by way of example only, with reference to the accompanying drawings, in which:

FIG. 1 shows the nucleotide (SEQ ID NO: 5) and amino acid (SEQ ID NO: 6) sequence of the 39D10 heavy chain;

FIG. 2 shows the nucleotide (SEQ ID NO: 7) and amino acid (SEQ ID NO: 8) sequence of the 39D10 light chain;

Figure 7:
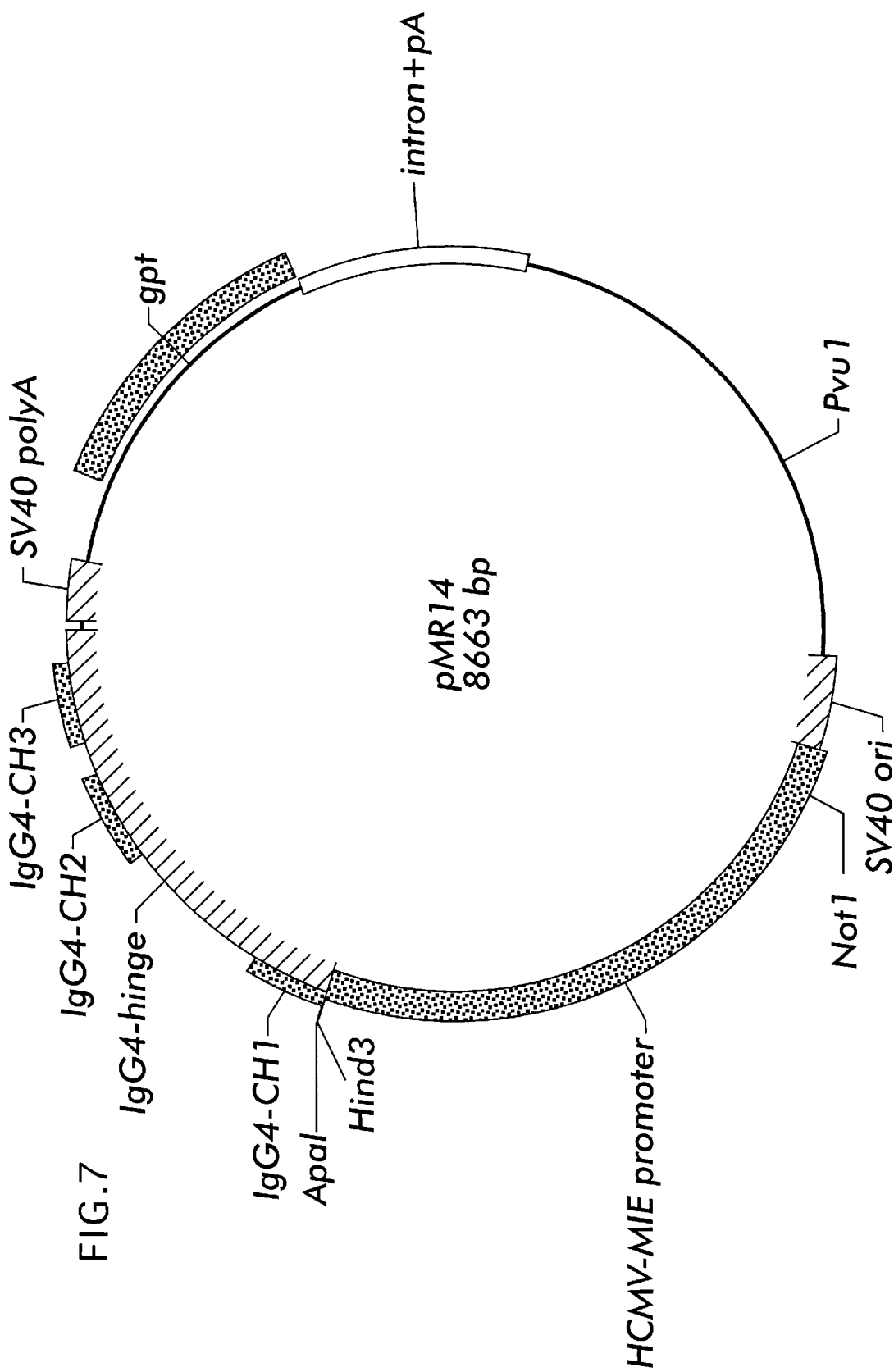
Figure 8:
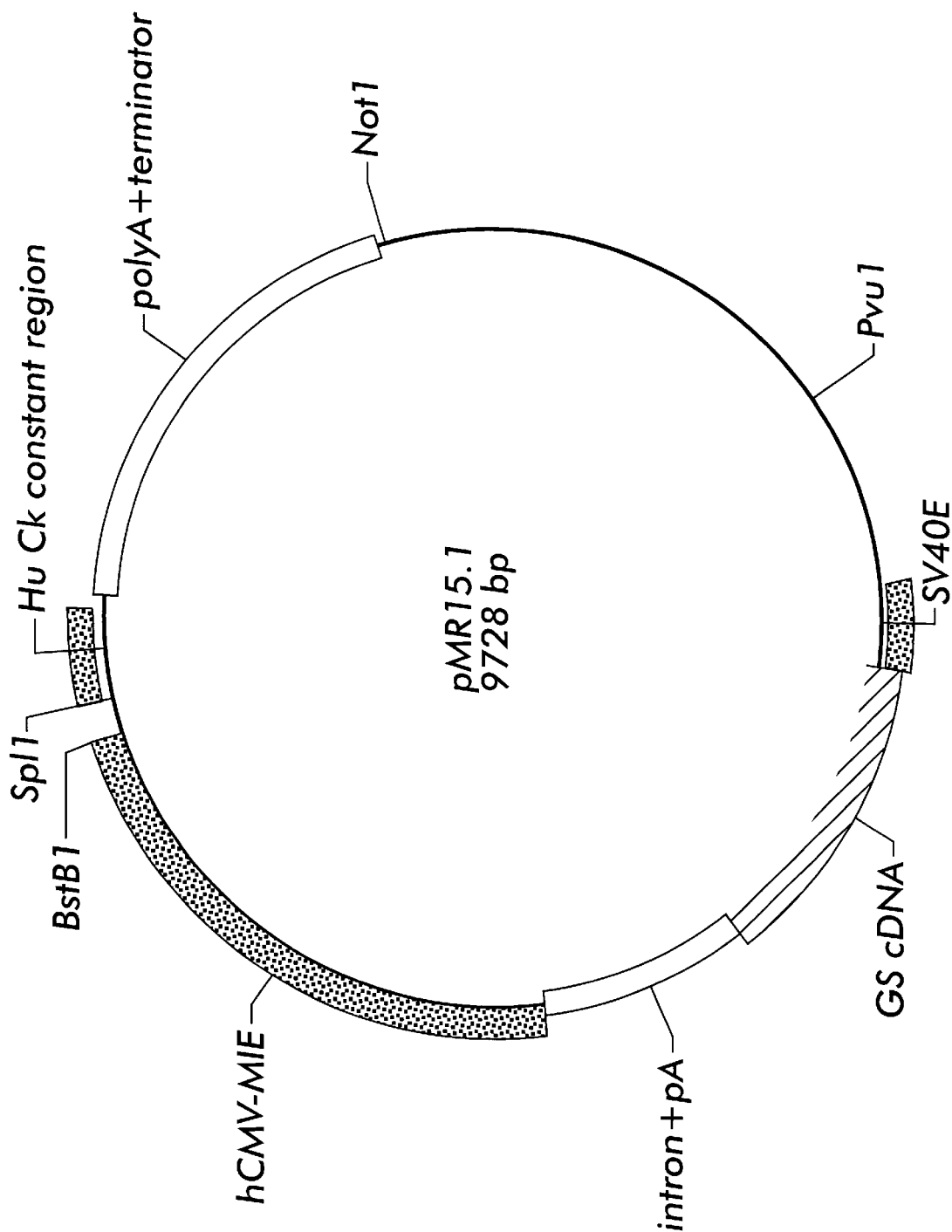
Figure 10:
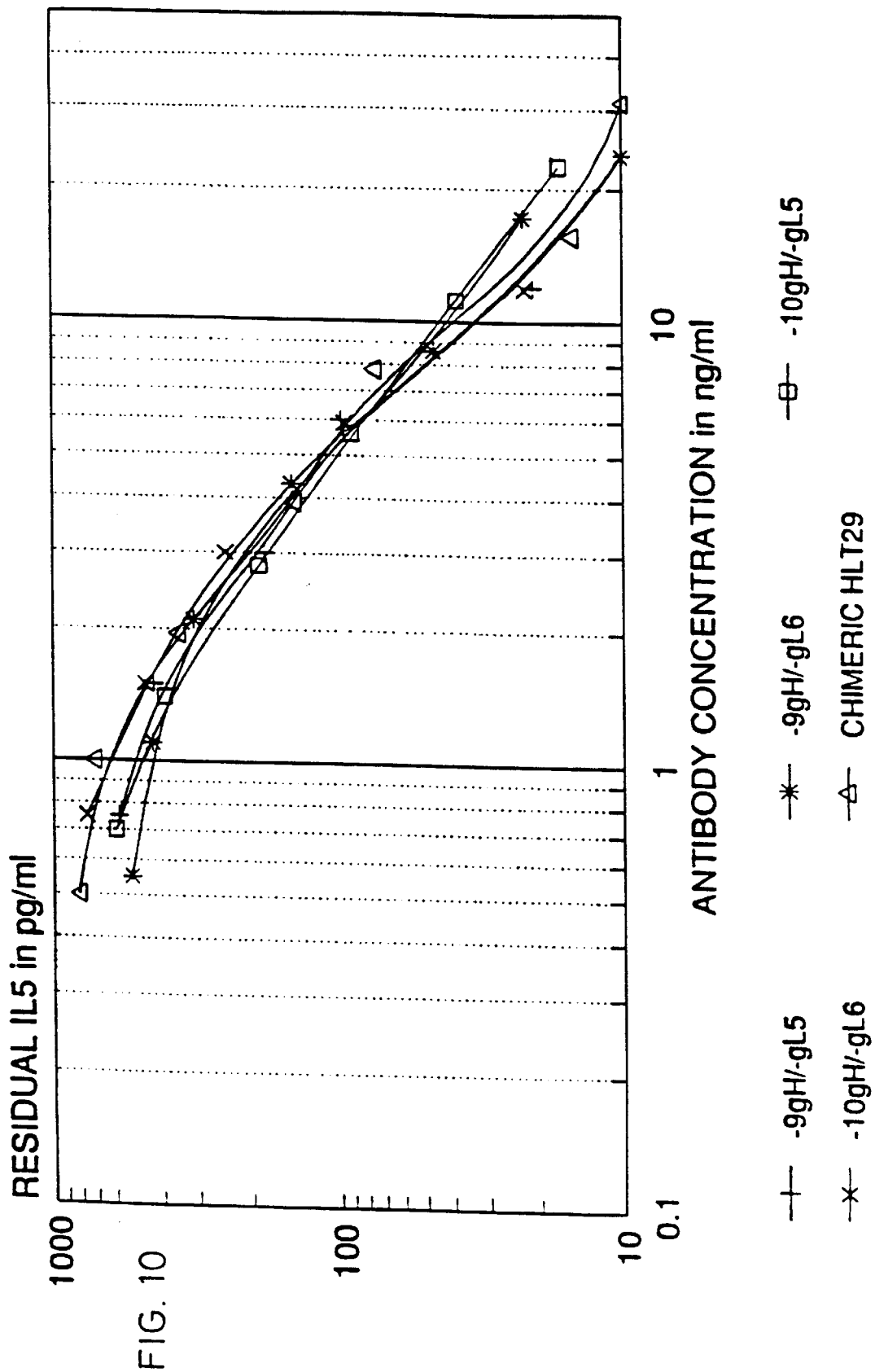
Figure 11:
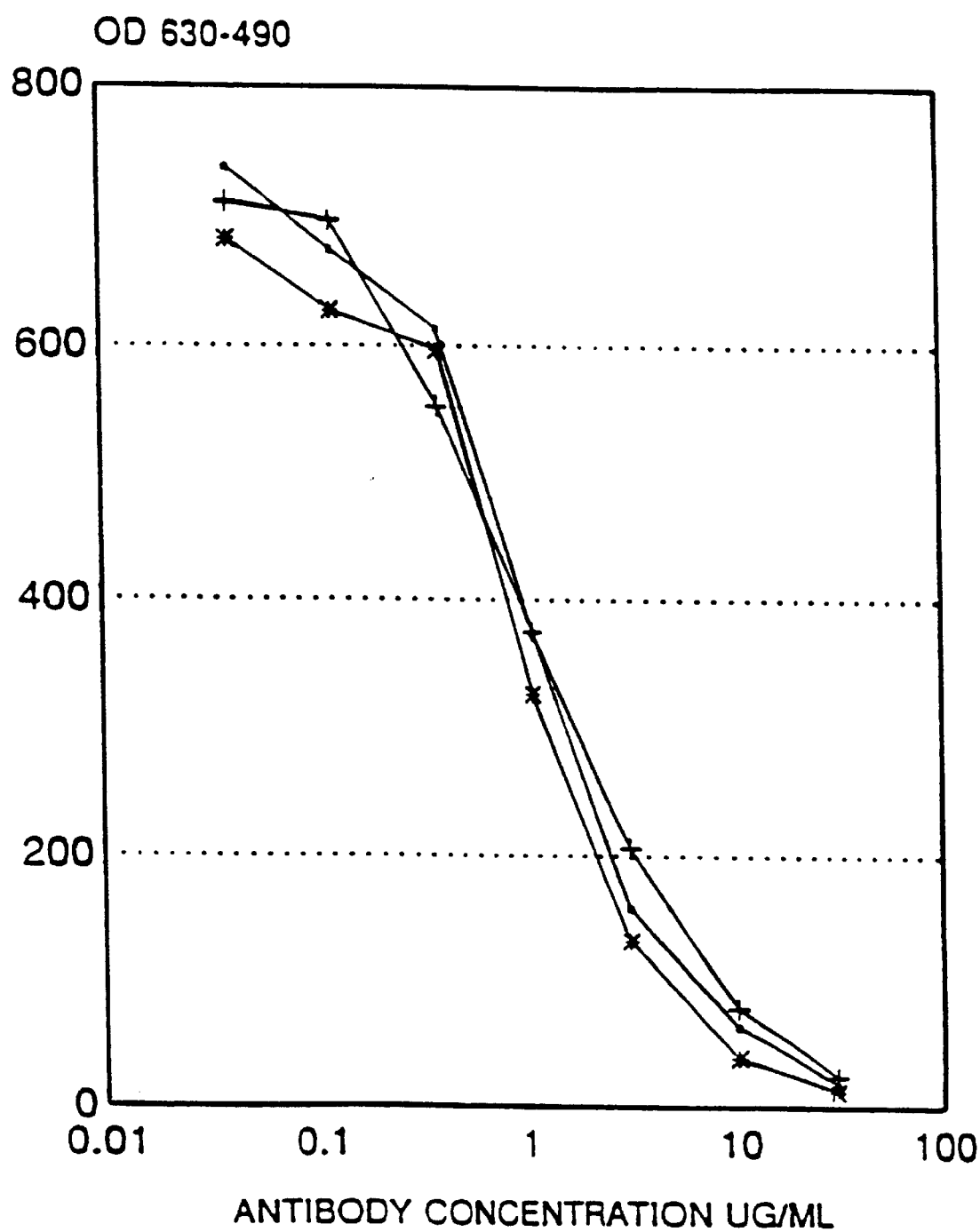
Figure 12:
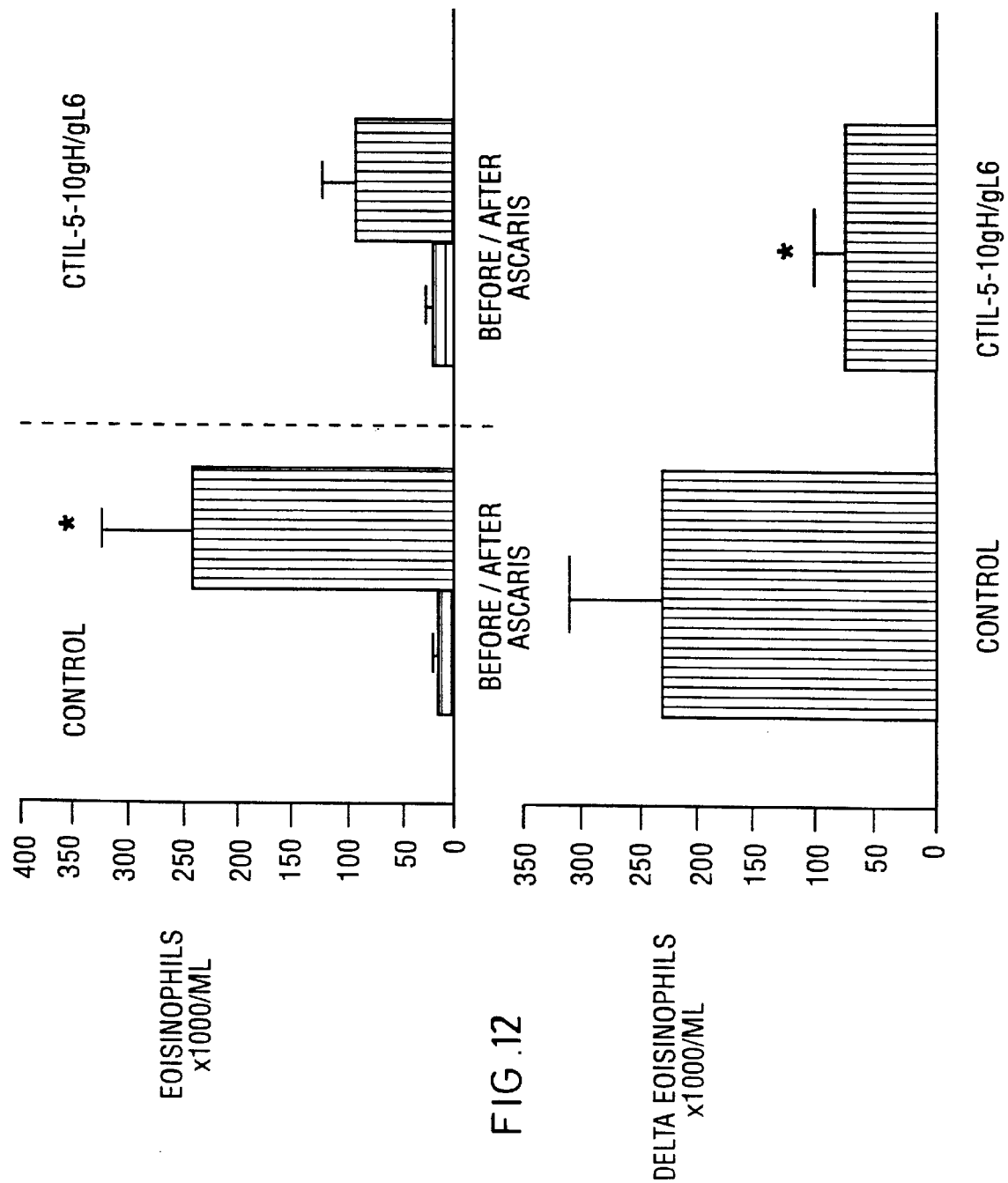

FIG. 3 shows the alignment of the 39D10 heavy chain variable domain framework regions 1 (SEQ ID NO: 10), 2 (SEQ ID NO: 12), 3 (SEQ ID NO: 14), and 4 (SEQ ID NO:16) with the light chain variable domain framework regions 1 (SEQ ID NO: 9), 2(SEQ ID NO: 11), 3(SEQ ID NO: 13), and 4 (SEQ ID NO: 15) of the consensus sequence of the human group I light chains, respectively;

FIG. 4 shows the alignment of the 39010 heavy chain variable domain framework regions 1 (SEQ ID NO:18), 2 (SEQ ID NO:20), 3 (SEQ ID NO:22), and 4 (SEQ ID NO:24) with the heavy chain variable domain framework regions 1 (SEQ ID NO: 17), 2 (SEQ ID NO: 19), 3 (SEQ ID NO:21), and 4 (SEQ ID NO:23) of the consensus sequence of the human group III heavy chains, respectively;

FIG. 5 shows the nucleotide (SEQ ID NO: 25) and amino acid (SEQ ID NO: 26) sequence of the CDR grafted anti-IL-5 light chain CTIL-5-gL6;

FIG. 6 shows the nucleotide (SEQ ID NO: 27) and amino acid (SEQ ID NO: 28) sequence of the CDR grafted anti-IL-5 heavy chain CTIL-5-10 gH;

FIG. 7 shows a map of plasmid pMR14;

FIG. 8 shows a map of plasmid pMR15.1;

FIG. 9 shows the affinity constants and association and disassociation rates of a chimeric 39D10 antibody and the CTIL-5-10gH\-gL6 antibody;

FIG. 10 shows a graph of the neutralisation of IL-5 in the TF1 assay by a panel of antibodies;

FIG. 11 shows the results of a competition assay for rat 39D10, a chimeric 39D10 antibody and the CTIL-5-10gH/gL6 antibody; and FIG. 12 shows the effect of CTIL-5-10gH/gL6 on monkey eosinophilia.

EXAMPLE

1. Material and Methods

39D10 is a rat monoclonal antibody raised against human IL-5. The genes for the variable domains of the heavy and light chains of 39D10 have previously been cloned (WO 93/16184) and the nucleotide and predicted amino acid sequences of these domains are shown in FIGS. 1 and 2. Because of the strategy used in the cloning of the variable domain of the 39D10 heavy chain, the first five amino acids of the framework regions are unknown. However, a heavy chain was available which contained the leader sequence and the first five amino acids of framework 1 from the antibody YTH 34.5HL, Riechmann et al, [Nature, 332, 323–327 (1988)].

2. Molecular Biology Procedures

The molecular biology procedures used were as described in Maniatis et al. [Molecular Cloning: A Laboratory Manual, Second Edition, Vols 1 to 3, Cold Spring Harbor Laboratory Press (1989)].

3. Construction of Recombinant Heavy an Light Chain Genes

Heavy Chain

A heavy chain Vh region was generated by PCR using the oligonucleotides R3601 and R2155. The sequences of these are:

R3601 5'CCGCGCAAGCTTGCCCCCACCATGAAG(A,T)TGTGGTTAAACTCGGTTTT3'(SEQ ID NO: 1)

R2155 5'GCAGATCGGCCCTTCGTTGAGGCTG(A,C)(A,G)GAGAC(G,T,A)GTGA3'(SEQ ID NO: 2)

The reaction mixture (100 µl) contained 10 mM Tris-HCl pH 8.3, 1.5 mM MgCl, 50 mM KCl, 0.01% w/v gelatin, 0.25 mM of each deoxyribcnucleoside triphosphate, 0.1 µg 39D10 heavy chain DNA, 6 pmoles of R3601 and R2155 and 0.25 units Taq polymerase. The reaction mixture was heated at 94° C. for 5 minutes and then cycled through 94° C. for 1 minute, 55° C. for 1 minute and 72° C. for 1 minute. After 30 cycles, the reaction was extracted with an equal volume of phenol/chloroform (1:1 v/v), then with chloroform before being precipitated by the addition of 2.5 volumes of ethanol. The PCR product was dissolved in the appropriate buffer, digested with HindIII and ApaI, purified on an agarose gel and ligated into the vector pMR14 (FIG. 7) which had also been digested with HindIII and ApaI. Following transformation into E. coli LM1035, colonies were grown overnight and plasmid DNA analysed for Vh inserts. The nucleotide sequence of the Vh region in plasmid, pARH1217, is shown in FIG. 1 (SEQ ID NO: 5).

Light Chain

A Vl light chain gene was generated from the original Vl, as described in WO 93/16134, clone by PCR with the oligonucleotides R3585 and R3597. The sequences of these are:

R3585 5'GGACTGTTCGAAGCCGCCACCATGAGTGTGCT CACTCAGGTCCT3'(SEQ ID NO: 3)

R3597 5'GGATACAGTTGGTGCAGCATCCGTACGTTT3' (SEQ ID NO: 4)

PCR was carried out as described above. The PCR product was digested with the enzymes BstBI and SplI and, after purification, ligated into pMR15.1 (FIG. 8) that had previously been digested with the same enzymes.

A colony was identified, after transformation of E. coli LM1035, that contained a plasmid (pARHI215) with a Vl insert. The nucleotide sequence of the Vl insert is shown in FIG. 2.

CDR Grafting of 39D10

Light Chain

In order to decade on the most appropriate human acceptor frameworks for the CDR loops of 39D10, the amino acid sequence of frameworks 1–3 of 39D10 were compared with those of known human kappa light chains, 39D10 was found to be most homologous to human group I light chains. Based on this, it was decided to use the human group I germ line frameworks for the CDR grafting. The homologies between these sequences are shown in FIG. 3. Also shown is the homology between the framework 4 regions of 39D10 and the consensus sequence of known human group I light chains. The residues in 39D10 that differ from the human consensus sequence are underlined. The contribution that these residues might make to antigen binding was analysed and two genes were constructed for the CDR grafted light chain. These were CTIL-5-gL5 and CTIL-5-gL6 in which, as well as the CDR residues, either residues 22, 68 and 71 or residues 68 and 71 were also from 39D10 respectively. The nucleotide and amino acid sequences of CTIL-5-gL6 are shown in FIG. 5.

Heavy chain

CDR grafting of the 39010 heavy chain was carried out as described for the light chain. The framework regions of 39D10 were found to be most homologous to those of human group III antibodies and, consequently, the consensus sequence of the frameworks of the human group III germ line genes was used to accept the CDts of the 39D10 heavy chain. As before, the consensus sequence for human group III framework 4 regions was also chosen. A comparison of these sequences is shown in FIG. 4 with the residues in 39D10 that differ from the human consensus sequence underlined.

Analysis of the framework residues in 39D10 that might influence antigen binding was carried out and, based on him, two genes, CTIL-5-9gH and CTIL-5-10gH, where constructed in which either residues 23, 24, 27 to 30, 37, 49, 73 and 76 to 78 or residues 24, 27–30, 37, 49, 73, 76 and 78 respectively were from 33D10. The nucleotide (SEQ ID NO: 27) and amino acid (SEQ ID NO: 28) sequences of CTIL-5-10gh is shown in FIG. 6.

Expression and Bioactivity of Anti-IL-5 Antibodies

Chimeric (rat/human) and CDR grafted 39D10 were produced for biological evaluation by transient expression of the heavy and light chain pairs after co-transfection into Chinese Hamster Ovary (CHO) cells using calcium phosphate precipitation.

On the day prior to transfection, semi-confluent flasks of CHO-L761h cells (Cockett et al., Nucl. Acids. Res., 19, 319–325, 1991) were trypsinised, the cells counted and T75 flasks set up each with $10^7$ cells. On the next day, the culture medium was changed 3 hours before transfection. For transfection, the calcium phosphate precipitane was prepared by mixing 1.25 ml of 0.25M $CaCl_2$ containing 50 μg of each of heavy and light chain expression vectors with 1.25 ml of 2×HBS (16.36 g NaCl, 11.9 gm HEPES and 0.4 g $Na_2HPO_4$ in 1 liter water with the pH adjusted to 7.1 with NaOH) and adding immediately into the medium of the cells. After 3 hours at 37° C. in a $CO_2$ incubator, the medium and precipitate were removed and the cells shocked by the addition of 15 ml 15% glycerol in phosphate buffered saline (PBS) for 1 minute. The glycerol was removed, the cells washed once with PBS and incubated for 48–96 hours in 25 ml medium containing 10 mM sodium butyrate. Antibody was purified from the culture medium by binding to and elution from protein A—Sepharose. Antibody concentration was determined using a human Ig ELISA (see below).

Elisa

Antibody express ion was assessed by transfecting pairs of heavy and light chain genes into CHO cells and, after three days incubation, measuring the amount of antibody accumulating in the culture medium by ELISA.

For the ELISA, Nunc ELISA plates were coated overnight at 4° C. with a F(ab')$_2$ fragment of a polyclonal goat anti-human Fc fragment specific antibody (Jackson Immunoresearch, code 109-006-098) at 5 μg/ml in coating buffer (15 mM sodium carbonate, 35 mM sodium hydrogen carbonate, pH6.9) Uncoated antibody was removed by washing 5 times with distilled water. Samples and purified standards to be quantitated were diluted to approximately 1 μg/ml in conjugate buffer (0.1M Tris-HCl pH7.0, 0.1M NaCl, 0.2% v/v Tween 20, 0.2% w/v Hammersten casein). The samples were titrated in the microtitre wells in 2-fold dilutions to give a final volume of 0.1 ml in each well and the plates were incubated at room temperature for 1 hour with shaking. After the first incubation step, the plates were washed 10 times with distilled water and then incubated for 1 hour as before with 0.1 ml of a mouse monoclonal anti-human kappa (clone GD12) peroxidase conjugated antibody (The Binding Site, code MP135) at a dilution of 1 in 700 in conjugate buffer. The plate was washed again and substrate solution (0.1 ml) added to each well. Substrate solution contained 150 μl N,N,N,N-tetramethylbenzidine (10 mg/ml in DMSO), 150 μl hydrogen peroxide (30% solution) in 10 ml 0.1M sodium acetate/sodium citrate, pH6.0. The plate was developed for 5–10 minutes until the absorbence at 630 nm was approximately 1.0 for the top standard. Absorbence at 630 nm was measured using a plate reader and the concentration of the sample determined by comparing the titration curves with those of the standard.

Determination of Affinity Constants for Anti-IL-5 Antibodies

Affinities of the chimeric and CDR grafted anti-IL-5 antibodies were determined using Biospecific Interaction Analysis (BIA). Antibodies were produced in CHO cells by transfection of combinations of heavy and light chain genes and purified from culture supernatants on Protein A Sepharose. For affinity measurements, a polyclonal anti-human Fc antibody was bound to the Pharmacia Biosensor chip (12150 relative response units, RU) and used to capture anti-IL-5 which was passed over the chip at 5 μg/ml in 10 mM HEPES, 0.15M SaCl, 3.4 mM EDTA, pH7.4. The amount of anti-IL-5 captured for each run was approximately 1600 RU. Recombinant human TL-5 was then passed over the Sensorchip at various concentrations (0.6 to 5 μg/ml) in the above buffer. The Sensorchip was cleaned after each run with 100 mM HCl and 100 mM orthophosphoric acid to remove bound IL-5 and antibody, The sensorgrams generated were analysed using the kinetics software available with the BIAcore machine.

Values for the affinity constants and association and dissociation rates of two antibodies, chimeric 39D10 and CTIL-5-10gH/-gL6, were determined. The results are shown in FIG. 9. It can be seen that chimeric 39D10 has an extremely high affinity for human IL-5 and that this value has been reproduced in CTIL-5-10gH/-gL6.

Activity of Anti-IL-5 Antibodies in in vitro Bioassay

The activities of various CDR grafted antibodies were compared with that of chimeric 39D10 in an in vitro bioassay using TF1 cells. TF1 is an erythroleukemic cell line that requires GM-CSF for growth. GM-CSF can be replaced by IL-5 but in this instance the cells only survive and do not proliferate. However the dependence on IL-5 for survival means that TF1 cells can be used in a bioassay to compare the activities of various anti-IL-5 antibodies.

Neutralisation by anti-IL-5 antibodies was measured using a constant amount of IL-5 (2 ng/ml) and variable amounts of antibody incubated with $5 \times 10^4$ cells per well in 96 flat bottomed plates for 3 days. For the last 4 hours, cells are cultured in the presence of 500 μg/ml Thiazolyl blue (MIT). This dye is converted into an insoluble purple form by mitochondrial enzymes in viable cells. The insoluble material was dissolved by incubating overnight after addition of 100 μl of 50% dimethyl formamide, 20% SDS pH4.7 and the amount of dye taken up determined spectrochotometrically. The levels of bioactive IL-5 remaining in the presence of the antibodies is extrapolated from a standard curve relating dye uptake to IL-5 concentration.

The activities of various combination of heavy and light chains were evaluated using the TF1 bioassay. The results are shown in FIG. 10. It can be seen that all combinations of CDR grafted heavy and light chains produce antibodies that are equipotent with chimeric 39D10. These results indicate that neither residue 22 in the light chain nor residues 23 or 78 in the heavy chain are required to be 39D10 specific for optimal binding. The combination with the fewer 39010 specific residues is therefore CTIL-5-10gH/-gL6.

Activity of Anti-IL-5 Antibodies in Competition Assays

Recombinant human IL-5 was diluted to 1 μg/ml in phosphate buffered saline (PBS) and 100 μl aliquots added to microtitre plates (Costar Amine Binding plates) and incubated overnight at 4° C. Plates were washed three times with PBS containing 0.5% Tween 20 and any remaining active sites blocked with 2% bovine serum albumin (BSA) in PBS for 30 minutes. The plates were then aspirated and tapped dry. To compare the relative binding activity of the parent rat antibody (39010) with chimeric and grafted antibodies, serial dilutions were prepared of each anti-IL-5 antibody in PBS/1% BSA and 50 μl added to duplicate wells followed immediately by 50 μl 39D10-biotin conjugate at 0.125 μg/ml. The assay was incubated for 2 hours at room temperature with agitation and then washed twice with PBS. Horseradish-peroxidase conjugated to streptavidin (1 μg/ml) was added to all wells and incubated for a further 30 minutes. Plates were washed four times and 100 μl tetramethyl benzidine (TMB) substrate added. Colour development was read at 630 nm (reference 490 nm) and OD (630–490) was plotted against log (10) antibody concentration.

When the activities of rat 39D10, chimeric 39D10 and CTIL-5-10gH/gL6 were compared in the above competition assay, the results shown in FIG. 11 were obtained. All three antibodies competed equally well with biotinylated-39D10 for binding to IL-5, indicating that the CDR loops of 39D10 had been successfully transferred to the human frameworks Effect of Anti-IL-5 Antibody on Monkey Eosinophilia Anti-IL-5 antibody (CTIL-5-10gH/gL6) was tested in a monkey system which models asthmatic conditions (see Mauser, P. J. et al., *Am. J Resp. Crit. Care Med.,* 152:467–472, 1995). When administered, one hour before challenge with Agcaris, to responsive monkeys, CTIL-5-10gH/gL6 inhibits lung lavage eosinophilia 75% at a dose of 0.3 mg/kg i.v. This set of monkeys is not hyper-responsive to histamine so the effects of CTIL-5-10gH/gL6 on hyper-responsiveness could not be determined. Three months after this single dose, eosinophil accumulation in response to Ascaris challenge is still inhibited 75%.

In the allergic mouse, CTIL-5-10gH/gL6 inhibits pulmonary eosinophilia at 1 mg/kg i.p.

What is claimed is:

1. A DNA sequence encoding a composite heavy chain of a recombinant antibody molecule that specifically binds human Interleukin-5 antigen, said composite heavy chain comprising acceptor antibody heavy chain framework residues, said variable domain comprising corresponding donor residues from murine monoclonal 39D10 heavy chain variable region having the amino acid sequence shown in FIG. 1 (SEQ ID NO: 6) at residues 31–35, 50–65 and 95–102 and at framework residues 23, 24, 27–30, 37, 49, 73, 76, 77, and 78 according to the Kabat numbering system.

2. A DNA sequence encoding a composite light chain of a recombinant antibody molecule that specifically binds human Interleukin-5 antigen, said composite light chain comprising acceptor antibody light chain framework residues, said variable domain comprising acceptor antibody light chain framework residues, said variable domain comprising corresponding donor residues from murine monoclonal 39D10 light chain variable region having the amino acid sequence shown in FIG. 2 (SEQ ID NO: 8) at residues 24–34, 50–56 and 89–97 and at framework residues 22, 68, and 71 according to the Kabat numbering system.

3. A DNA sequence encoding a recombinant antibody molecule that specifically binds human Interleukin-5 antigen comprising a composite heavy chain and a composite light chain, said composite heavy chain and light chain having a variable domain comprising acceptor antibody framework residues, said variable domain comprising corresponding donor residues from murine monoclonal 39D10 heavy chain variable region having the amino acid sequence shown in FIG. 1 (SEQ ID NO: 6) at residues 31–35, 50–65 and 95–102 and at framework residues 23, 24, 27–30, 37, 49, 73, 76, 77, and 78, and corresponding donor residues from murine monoclonal antibody 39D10 light chain variable region having the amino acid sequence shown in FIG. 2 (SEQ ID NO: 8) at residues 24–34, 50–56 and 89–97 and at framework residues 22, 68, and 71 according to the Kabat numbering system.

4. A DNA sequence according to any one of claims 1–3, wherein the acceptor residues for the composite heavy chain are human group III heavy chain residues, and the acceptor residues for the composite light chain are human group I light chain residues.

5. A DNA sequence encoding a recombinant antibody molecule having affinity for human IL-5 antigen, comprising the heavy chain variable region amino acid sequence shown in FIG. 6 (SEQ ID NO: 28), and the light chain variable region amino acid sequence shown in FIG. 5 (SEQ ID NO: 26).

6. A cloning or expression vector containing a DNA sequence according to any one of claims 1–3 and 5.

7. A host cell transformed with a DNA sequence according to any one of claims 1–3 and 5.

8. A process for the production of an anti-Interleukin 5 antibody comprising expressing a DNA sequence according to any one of claims 1–3 and 5 in a transformed host cell.

* * * * *